United States Patent [19]
Yamauchi et al.

[11] Patent Number: 5,627,306
[45] Date of Patent: May 6, 1997

[54] OXYGEN CONCENTRATION SENSOR

[75] Inventors: Masanobu Yamauchi, Kariya; Isao Watanabe, Nagoya, both of Japan

[73] Assignee: Nippondenso Co., Ltd., Kariya, Japan

[21] Appl. No.: 605,917

[22] Filed: Feb. 23, 1996

[30] Foreign Application Priority Data

Mar. 3, 1995 [JP] Japan .................................. 7-070758

[51] Int. Cl.$^6$ .......................... H01C 07/00; G01N 31/12; G01N 27/26
[52] U.S. Cl. .................... 73/23.2; 73/23.32; 73/31.01; 73/24.04; 204/424; 204/426
[58] Field of Search ....................... 73/23.2, 23.31, 73/23.32, 31.01, 24.04; 204/424, 425, 426

[56] References Cited

U.S. PATENT DOCUMENTS

| | | | |
|---|---|---|---|
| 4,308,518 | 12/1981 | Hattori et al. | 338/34 |
| 4,505,807 | 3/1985 | Yamada | 204/425 |
| 4,532,492 | 7/1985 | Esper et al. | 338/34 |
| 4,559,126 | 12/1985 | Mase et al. | 204/425 |
| 4,824,548 | 4/1989 | Iino et al. | 204/406 |
| 4,883,643 | 11/1989 | Nishio et al. | 422/94 |
| 4,897,174 | 1/1990 | Wana et al. | 204/425 |
| 5,031,445 | 7/1991 | Kato et al. | 73/23.31 |
| 5,039,972 | 8/1991 | Kato et al. | 338/34 |
| 5,421,984 | 6/1995 | Saito et al. | 204/426 |
| 5,467,636 | 11/1995 | Thompson et al. | 73/23.31 |

*Primary Examiner*—Hezron E. Williams
*Assistant Examiner*—J. David Wiggins
*Attorney, Agent, or Firm*—Cushman, Darby & Cushman IP Group of Pillsbury Madison & Sutro LLP

[57] ABSTRACT

In an oxygen gas sensor having a variable electrical characteristic dependent upon ambient oxygen concentration, a ceramic holding member having a hole for holding a plate sensor sensor element is disposed in a housing with the element inserted into the housing. During sensor assembly, powder is filled under pressure in the housing between a pressurized member and the ceramic holding member. The ceramic holding member has an inclined surface descending directly from an upper opening end of the holding hole to form an obtuse angle between the sensor element and the inclined surface, so that the powder can flow on the inclined surface smoothly during the powder filling and powder compressing operations. By taking this construction it is possible to provide an oxygen concentration sensor with no cracking of the element and easy mounting of the sensor element to the housing.

14 Claims, 10 Drawing Sheets

OXYGEN CONCENTRATION SENSOR

CROSS REFERENCE TO RELATED APPLICATIONS

The present application is based on and claims priority from Japanese Patent Application Hei 7-70758, filed on Mar. 3, 1995, the content of which is incorporated herein by reference.

BACKGROUND OF THE INVENTION

1. Field of the Invention

The present invention relates to an oxygen concentration sensor used for air-fuel ratio control of an automobile engine.

2. Description of Related Art

A conventional oxygen concentration sensor, which is disclosed in U.S. Pat. No. 5,039,972 (corresponding to JPU 2-146363) and shown in FIGS. 15 and 16, includes a housing 10, a plate sensor element 12 inserted in housing 10, and a ceramic holding member 9 having a rectangular holding hole 90 for supporting plate sensor element 12 and disposed between housing 10 and plate sensor element 12.

Figure 15:
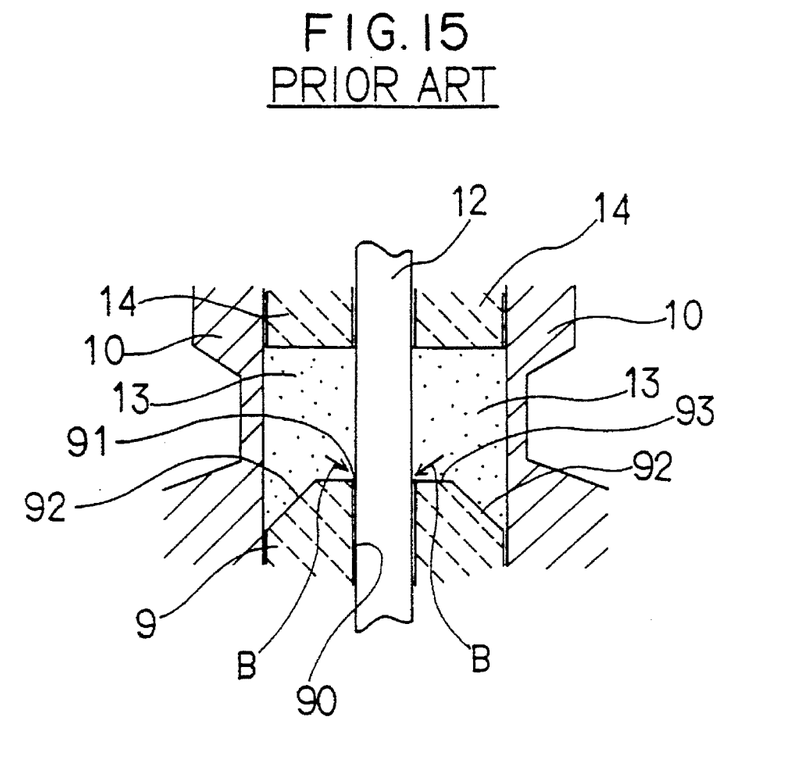
FIG. 15 is a cross sectional view illustrating the major part of an oxygen concentration sensor of a prior art.

Powder 13 filled and pressurized by a pressurizing member 14 placed above of housing 10 is disposed on ceramic holding member 9.

Figure 16:
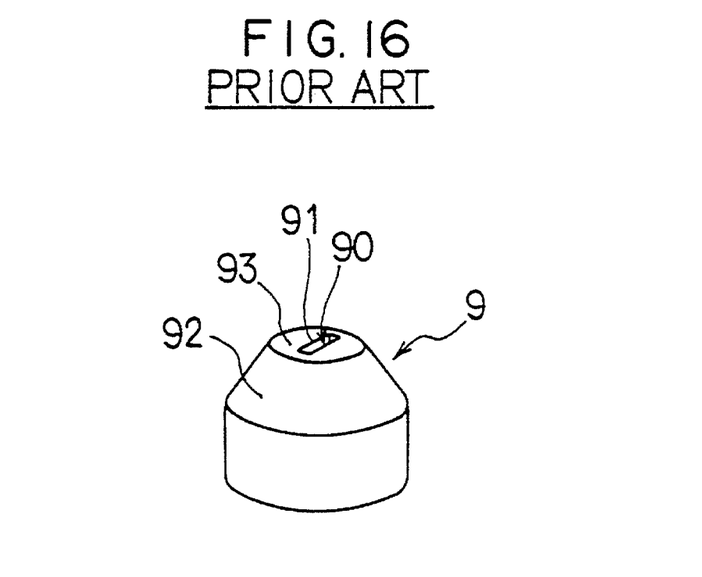
FIG. 16 is a perspective view illustrating a ceramic holding member of the above oxygen concentration sensor.

As shown in FIG. 16, ceramic holding member 9 has a tubular main body and holding hole 90 for holding plate sensor element 12. The circumference of an upper opening end 91 of holding hole 90 is a horizontal surface 93 and a tapered surface 92 is disposed around horizontal plane 93. As shown in FIG. 15, both horizontal plane 93 and conical surface 92 receive powder 13.

As shown in FIG. 15, however, at the time of filling and pressurizing powder 13 in a mounting process of plate sensor element 12, an impact is applied to the direction of arrows B around a boundary contacting plate sensor element 12, ceramic holding member 9 and powder 13, causing cracking of plate sensor element 12. The cracking of the element occurs more often when the impact is applied to a shorter (thinner) side of plate sensor element 12 as shown by an arrow T in FIG. 2B.

Therefore, the pressurizing speed has to be slowed down in order to prevent the cracking of the element in a conventional method. Although excessively large impact on plate sensor element 12 is avoided by this method, it takes a long time to mount plate sensor element 12. Controlling the pressurizing speed makes the mounting process of plate sensor element 12 more complicated. Furthermore, the conventional method is still ineffective in preventing force applied in the direction indicated by the arrow B to plate sensor element 12. Thus, the cracking of the element cannot be prevented completely.

SUMMARY OF THE INVENTION

In light of the above-described problem, a main object of the present invention is to provide an oxygen concentration sensor which is free from cracking of an element through a simple mounting process.

Another object of the present invention is to provide an oxygen concentration sensor in which the ceramic holding member has a inclined surface extending outward directly from an upper opening end of the holding hole to provide a moderate boundary along an interface between the inclined surface and the sensor element so that the powder can flow outward smoothly from the plate sensor element along the inclined surface.

The inclined surface is preferably a conical surface, and the holding hole has preferably upper opening sides in a same horizontal plane. The holding hole can be polygonal and the inclined surface can be formed around the upper opening sides of the polygonal holding hole.

The inclined surface can be formed only in a direction in parallel with a shorter side of the plate sensor element. It is possible to reduce the force applied to the direction which is more breakable in the plate sensor element so that the cracking of the element is prevented.

According to the feature described above, the pressurized powder can flow smoothly along the inclined surface, preventing stress from exerting on the plate sensor element.

It is also possible to use the upper opening end as a fixing surface when setting the holding member in a baking furnace, therefore, a freedom of positioning increases.

Also, as described in the above, in accordance with the decrease of defect caused by the cracking of the element, the productivity of oxygen concentration sensors is improved.

Also, the plate sensor element can be fixed in the housing with a pressure greater than that of before without increasing the stress, so that air tightness of the oxygen concentration sensor can be enhanced.

Since there is no need of slowing down the pressurizing speed for filling the powder, mounting speed of the sensor can be increased without sacrificing the precision of the plate sensor element.

BRIEF DESCRIPTION OF THE DRAWINGS

Other objects, features and characteristics of the present invention as well as the functions of related parts of the present invention will become clear from a study of the following detailed description, the appended claims and the drawings. In the drawings:

DETAILED DESCRIPTION OF THE PREFERRED EMBODIMENTS

First Embodiment

An oxygen concentration sensor according to the present invention will be explained with reference to FIG. 1 through FIG. 6.

Figure 1:
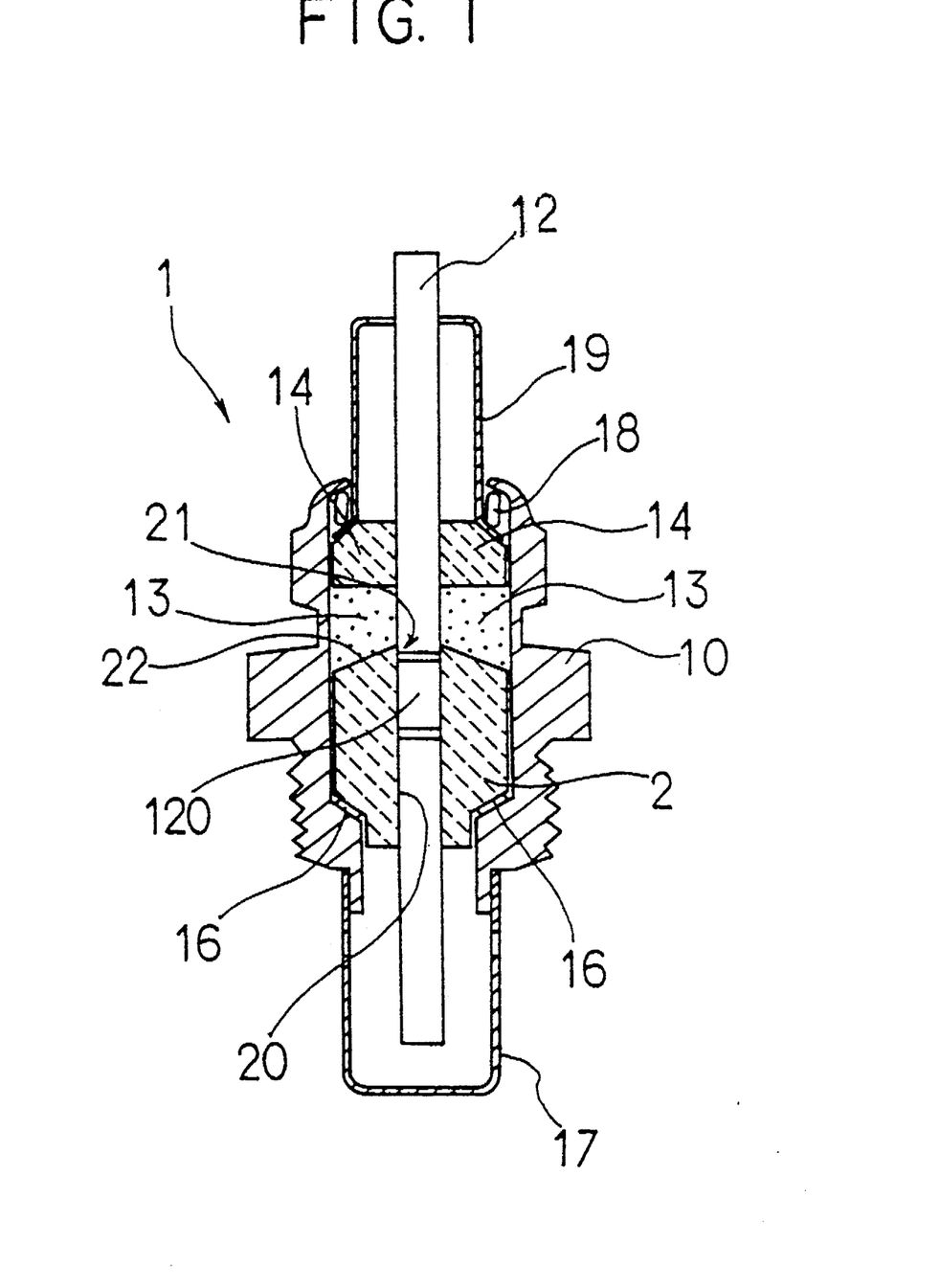
FIG. 1 is a cross-sectional view illustrating an oxygen concentration sensor according to a first embodiment of the present invention.

An oxygen concentration sensor 1, as shown in FIG. 1, includes a housing 16, a plate sensor element 12 inserted into housing 10 and a ceramic holding member 2 having a longitudinal holding hole 20 for supporting plate sensor element 12.

Figure 6:
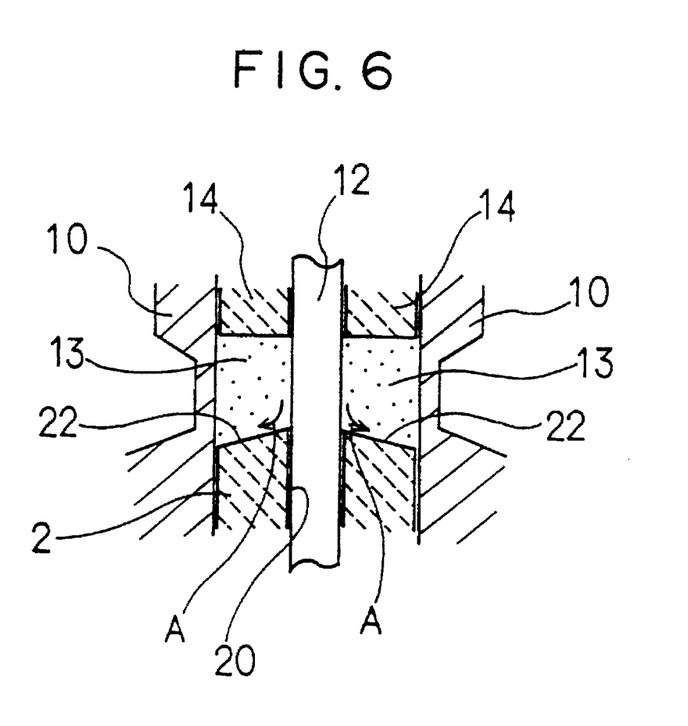
FIG. 6 is a cross-sectional view illustrating the major part of the oxygen concentration sensor according to the first embodiment.

Powder 13 is filled under pressure in a space between ceramic holding member 2 and a pressurizing member 14. Ceramic holding member 2 has a conical surface 22 which has an upper opening end 21 of holding hole 20 at the center thereof and receives pressurized powder 13. Conical surface 22 is a part of cone-shaped surface directly descending from upper opening end of holding hole 20 as shown in FIG. 3B and indicated by a dotted line in FIG. 5, so that the angle formed by plate sensor element 12 and conical surface 13 becomes obtuse and provides continuous flow surface for powder 13 as shown in FIG. 6.

Figure 2A:
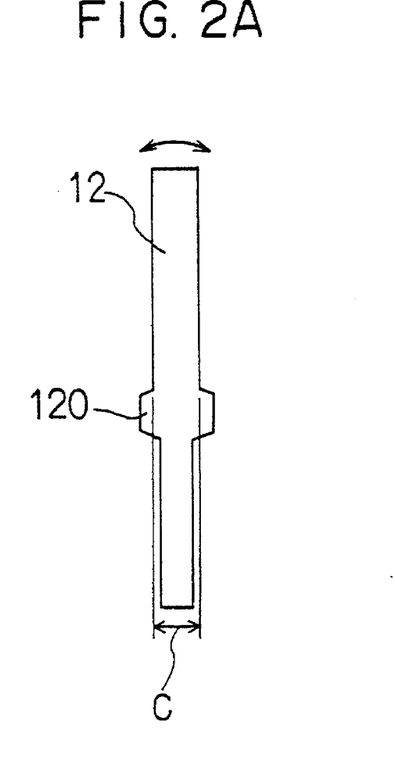
FIGS. 2A and 2B are a front view and a side view illustrating a plate sensor element of the oxygen concentration sensor according to the first embodiment respectively.
Figure 2B:
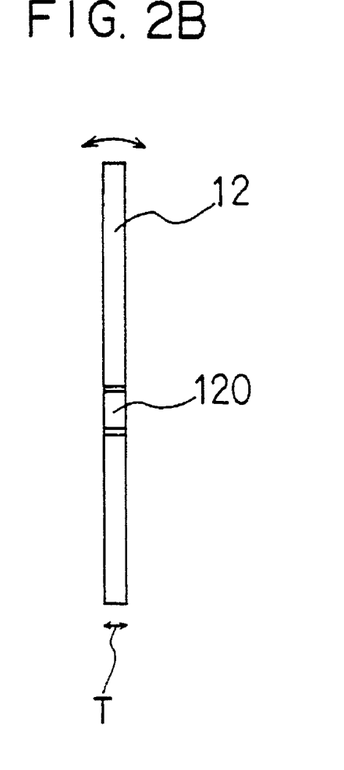

As shown in FIGS. 2A and 2B, plate sensor element 12 has a main body having a rectangular cross-section and a pair of flanges 120 which are supported by a receiving surface 25 of ceramic holding member 2 at a central portion of the main body.

An arrow C indicates a longer side or width-wise direction and an arrow T indicates a shorter side or thickness-wise direction respectively in plate sensor element 12.

Figure 3A:
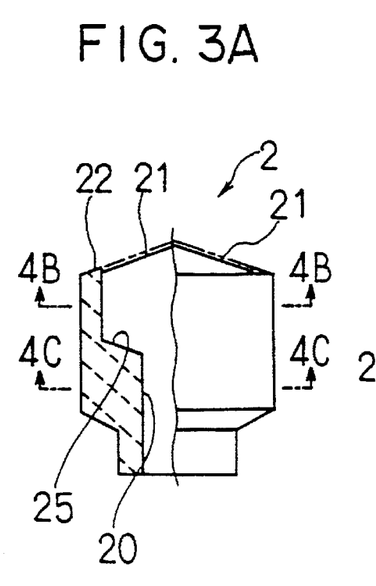
FIGS. 3A and 3B are partial cross-sectional front and side views illustrating a ceramic holding member according to the first embodiment.
Figure 3B:
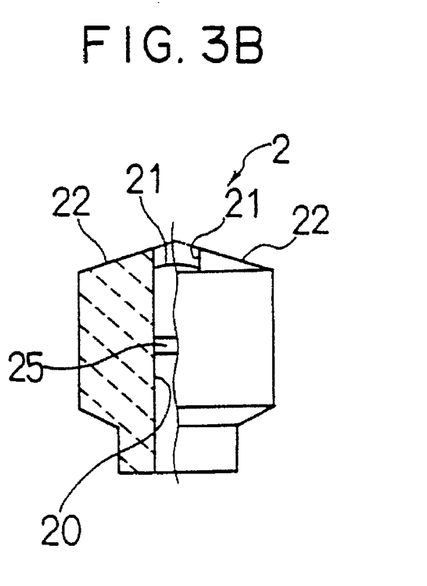
Figure 4A:
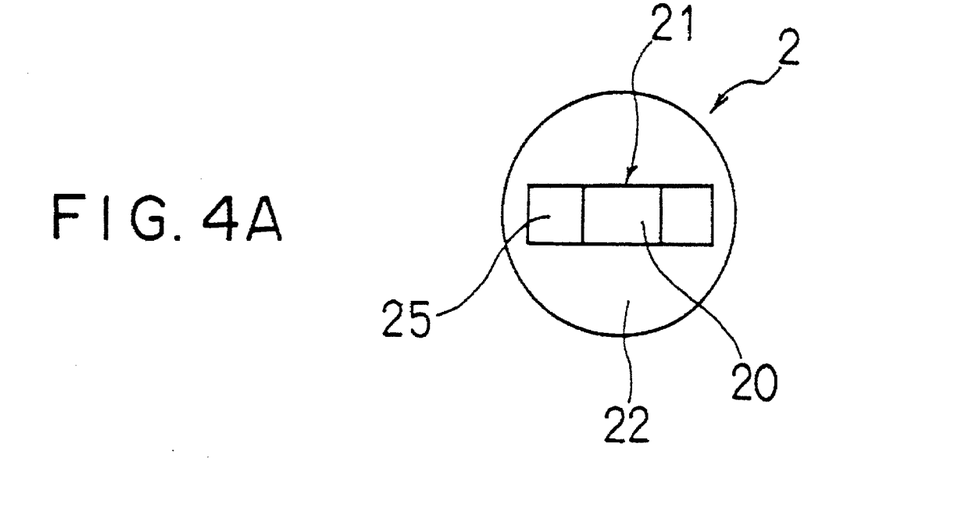
FIGS. 4A, 4B and 4C are a plan view, a sectional view taken along lines 4B—4B of FIG. 3 and a sectional view taken along the line 4C—4C of FIG. 3 of the ceramic holding member according to the first embodiment respectively.
Figure 4B:
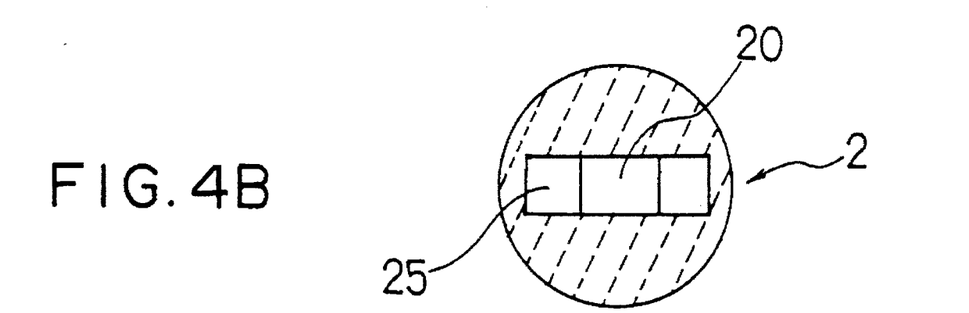
Figure 4C:
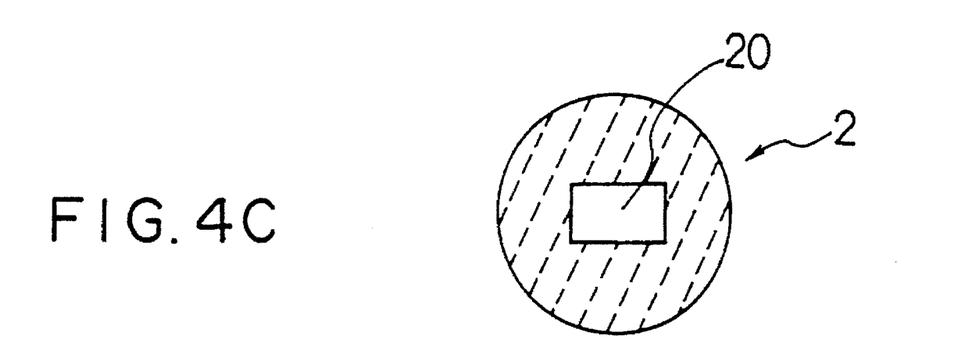
Figure 5:
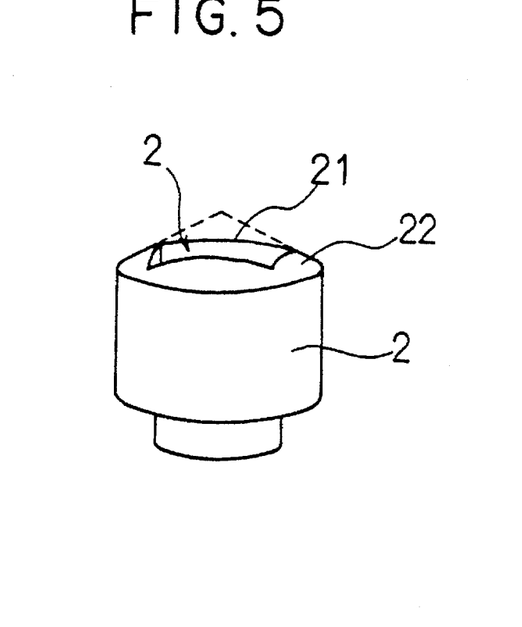
FIG. 5 is a perspective view illustrating the ceramic holding member according to the first embodiment.

As shown in FIGS. 3A and 3B, holding hole 20 is formed in the center of holding member to receive and hold plate sensor element 12. Receiving face 25 is formed to support flanges 120 of plate sensor element 12 as shown in FIG. 3B, FIG. 4A, FIG. 4B and FIG. 4C.

In FIG. 1, reference numerals 16, 17, 18 and 19 indicate respectively a cushion packing, a protecting cover, a metallic ring and a protection cover.

Next, a function and an effect according to the first embodiment is explained mainly with reference to FIG. 6.

Plate sensor element 12 is inserted into holding hole 20 of holding member 2, and powder 13 is filled in housing 10 and pressurized via pressurizing member 14 from outside. Powder 13 can be formed into a predetermined shape in advance and inserted in housing 10.

When pressure is applied on powder 13 via pressurizing member 14, powder 13 flows along conical surface 22 from the vicinity of plate sensor element 12 to the side of housing 10 smoothly as indicated by arrows A in FIG. 6. Therefore, high stress is not applied to plate sensor element 12.

As a result, plate sensor element 12 is fixed in holding hole 20 without receiving an excessively large impact thereto even at the time of pressurizing, thus cracking of the element is prevented.

Also, since stress applied to plate sensor element 12 decreases, plate sensor element 12 can be mounted in housing 10 with greater force so that a more air-tight oxygen concentration sensor can be obtained.

Furthermore, since the pressurizing speed of the powder pressurization step can be increased without increasing stress on the plate sensor element, the productivity is increased without reducing the precision of the sensor.

Figure 7:
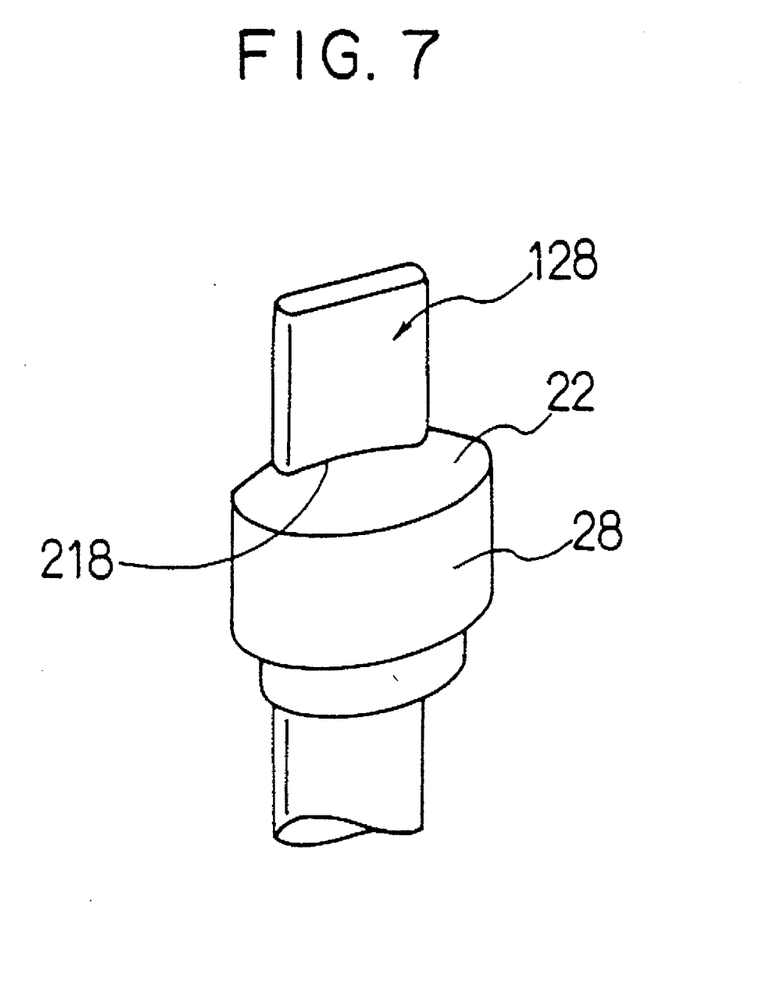
FIG. 7 is a perspective view illustrating the plate sensor element having an oval cross section and the ceramic holding member according to the first embodiment.
Figure 8A:
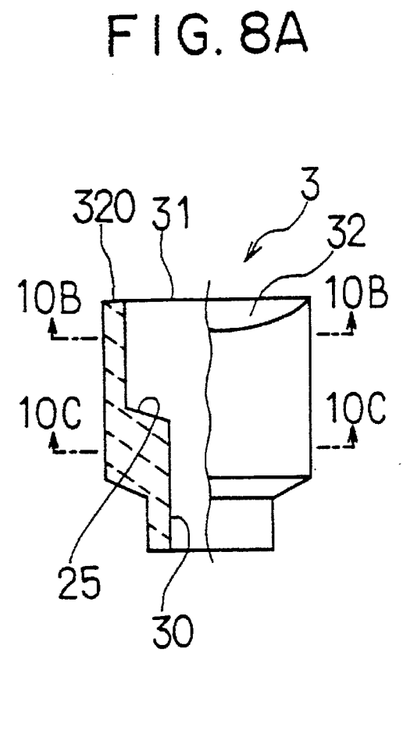
FIGS. 8A and 8B are a partial cross-sectional front and side views illustrating a ceramic holding member according to a second embodiment of the present invention.
Figure 8B:
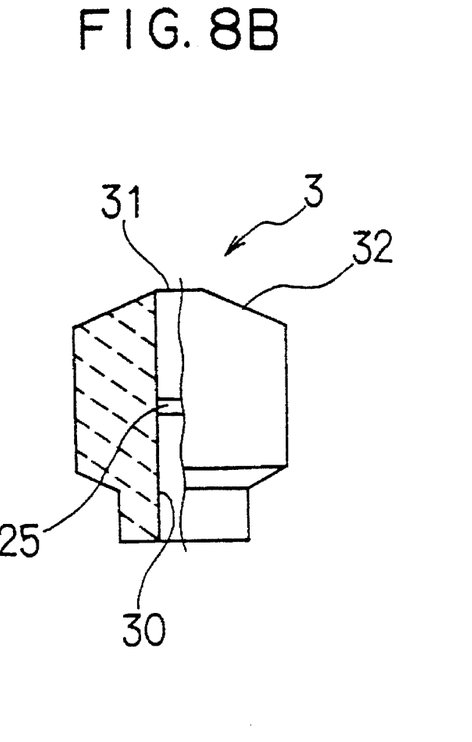
Figure 9:
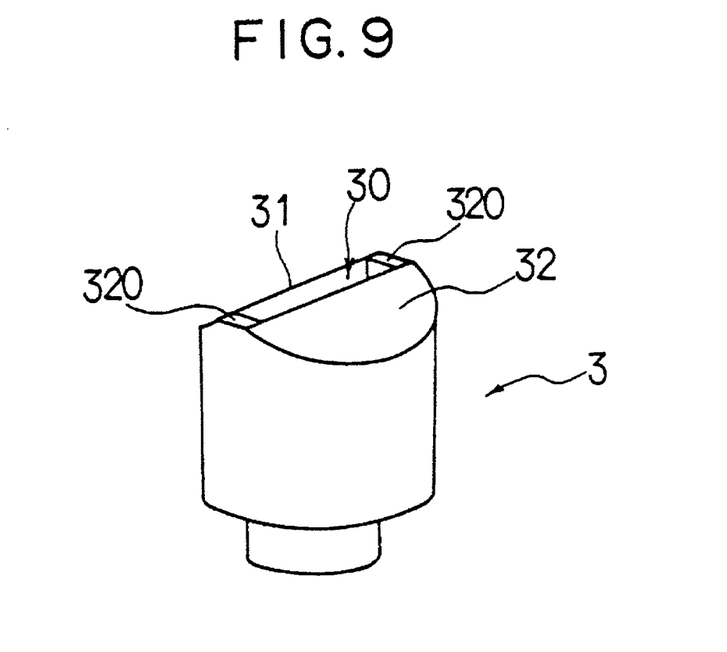
FIG. 9 is a perspective view illustrating the ceramic holding member according to the second embodiment.
Figure 10A:
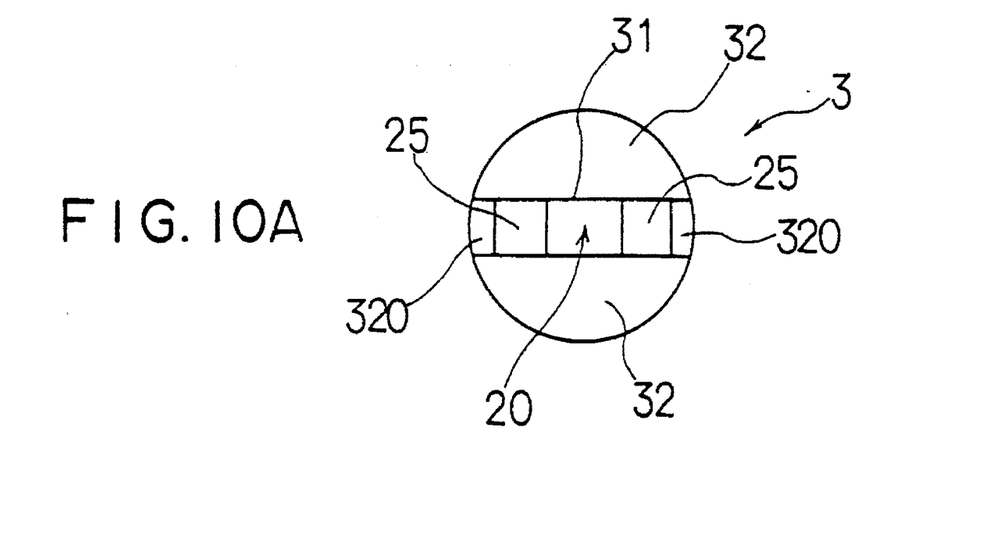
FIGS. 10A, 10B and 10C are a plan view, a cross-sectional view taken along lines 10B—10B of FIG. 8 and a sectional view taken along lines 10C—10C of FIG. 8 illustrating the ceramic holding member according to the second embodiment respectively.
Figure 10B:
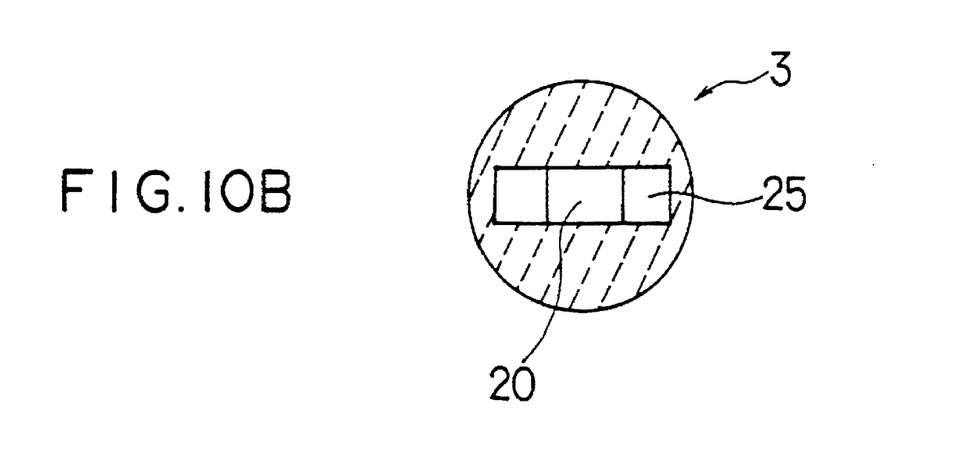
Figure 10C:
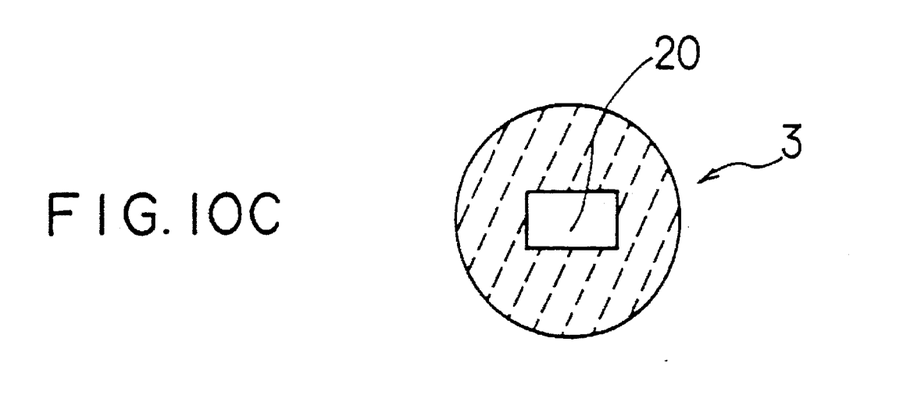

A ceramic holding member 28 with an oval hole 218 for supporting plate sensor element 128 having the same oval cross-section is shown in FIG. 7. An upper opening end of the holding hole is indicated as a reference numeral 218.

Second Embodiment

An oxygen concentration sensor according to a second embodiment of the present invention is described with reference to FIGS. 8 through FIGS. 10A, 10B and 10C.

A ceramic holding member 3 has inclined surfaces formed only in a direction (indicated by arrow T in FIG. 2B) parallel to the shorter side of holding hole 30. Longer sides of a rectangular upper opening end 31 of holding hole 30 are placed in a same horizontal plane as the shorter sides thereof.

Inclined surfaces 32 descend outward from opposite longer sides of upper opening end 31. On the other hand, horizontal surfaces 320 are formed on opposite shorter sides of the same. Both inclined surfaces 32 and horizontal surfaces 320 receive the pressurized powder.

Other elements are the same as described in the first embodiment.

The plate sensor element tends to be broken more in the direction parallel to the shorter side indicated by arrow T (thickness-wise) of FIG. 2B than in the direction parallel to the longer side indicated by arrow C of FIG. 2A when the plate sensor element is particularly thin. Therefore, in the oxygen concentration sensor having ceramic holding member 3, inclined surfaces 32 are formed to extend from the longer sides of upper opening end 31 so that powder can flow smoothly on the inclined surfaces to decrease the force applied to the thickness-wise direction.

Third Embodiment

Figure 11A:
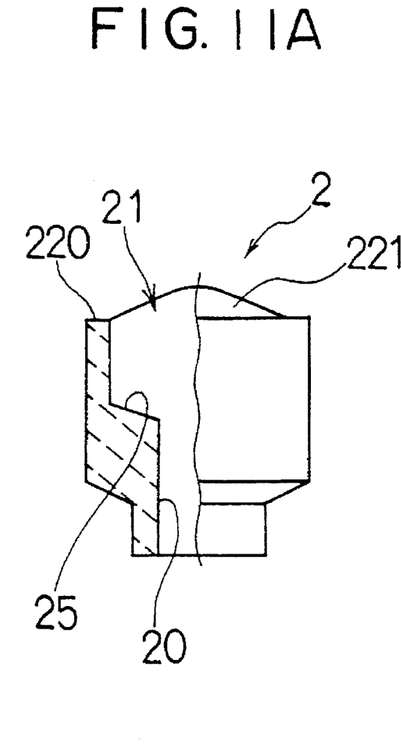
FIGS. 11A and 11B are a partial cross-sectional front and side views illustrating a ceramic holding member according to a third embodiment of the present invention.
Figure 11B:
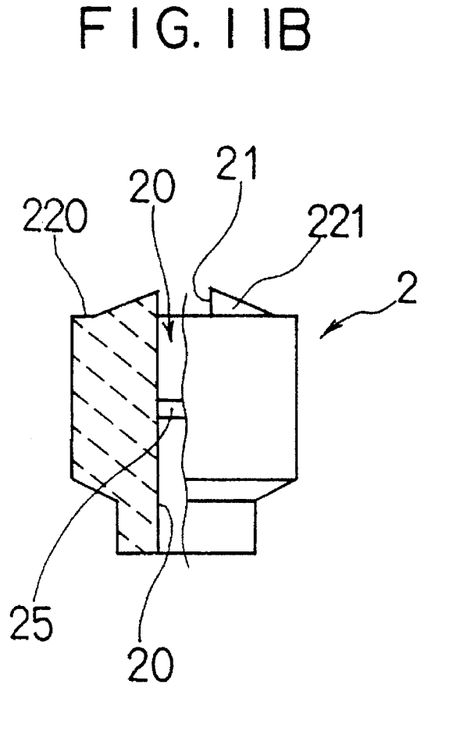
Figure 12:
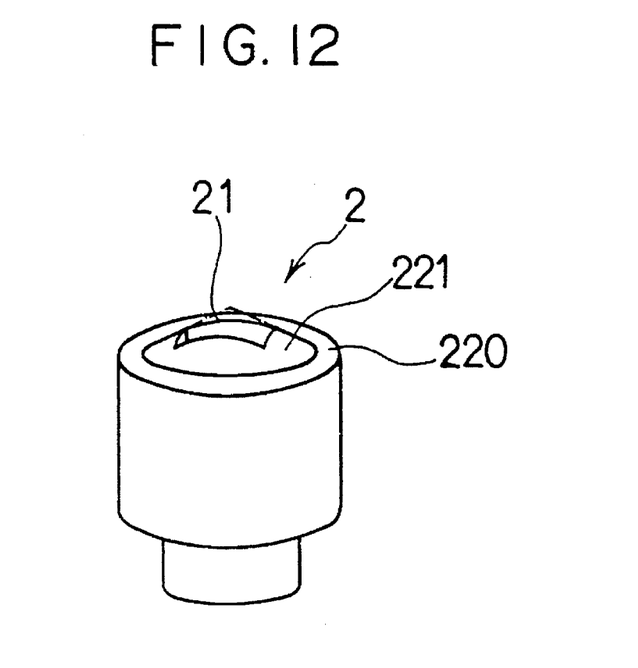
FIG. 12 is a perspective view illustrating the ceramic holding member according to the third embodiment.

In a ceramic holding member 2, a horizontal surface 220 is formed on an outer circumference of a conical surface 221 as shown in FIGS. 11A, 11B and FIG. 12.

Conical surface 221 is formed around an upper opening end 21 of ceramic holding member 2. Both conical and horizontal surfaces 221 and 220 receive the pressurized powder. Other elements are the same as described in the first embodiment.

In the oxygen concentration sensor having ceramic holding member 2 described in this embodiment, there is no portion which constitutes an acute angle and an even pressurized density of the powder can be obtained.

Fourth Embodiment

Figures 13A, 13B:
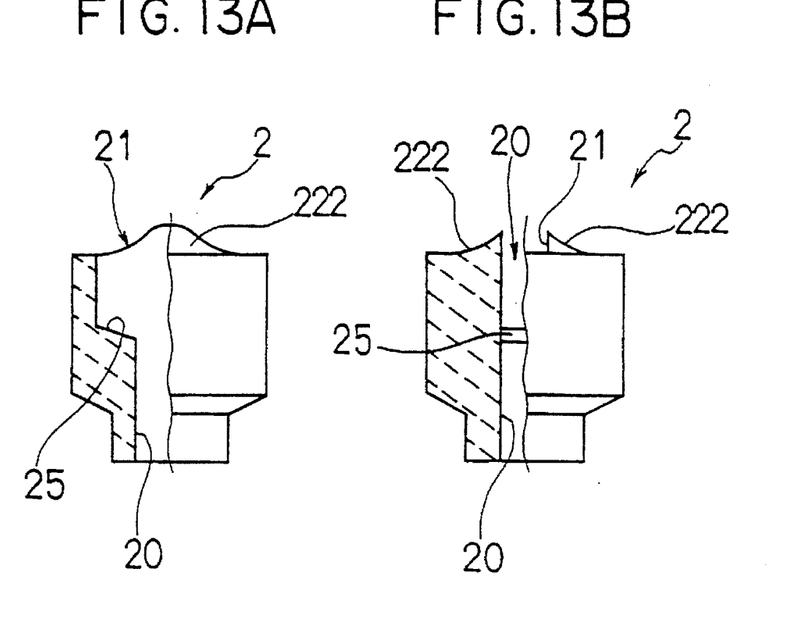
FIGS. 13A and 13B are a partial cross-sectional front and side views illustrating a ceramic holding member according to a fourth embodiment.

As shown in FIG. 13, parabolic surface 222 receives the pressurized powder. Other elements are the same as described in the first embodiment.

In the oxygen concentration sensor having ceramic holding member 2 according to this embodiment, the powder can be evenly filled as in the third embodiment.

Fifth Embodiment

Figure 14:
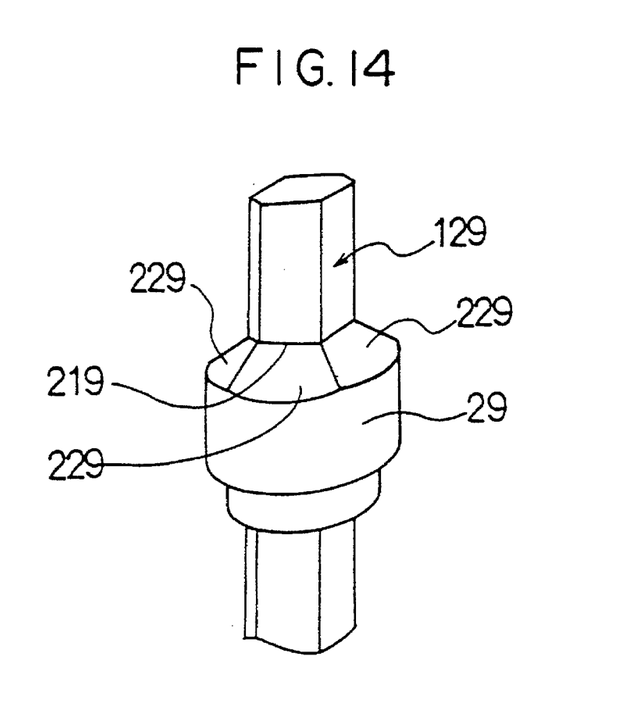
FIG. 14 is a perspective view illustrating a plate sensor element having a polygonal cross section supported by a ceramic holding member according to a fifth embodiment of the present invention.

As shown in FIG. 14, a ceramic holding member 29 having a holding hole of a polygonal cross-section for supporting a plate sensor element 129 which has the same polygonal cross section.

Inclined surfaces 229 are formed to descend from respective sides of upper opening end 219. Other elements are the same as described in the first embodiment.

Although the present invention has been fully described in connection with the preferred embodiments thereof with reference to the accompanying drawings, it is to be noted that various changes and modifications will become apparent to those skilled in the art. Such changes and modifications are to be understood as being included within the scope of the present invention as defined by the appended claims.

What is claimed is:

1. An oxygen concentration sensor constructed mainly of cylindrical parts along a central axis through said sensor including a housing, a longitudinally extending slab-shaped sensor element, a ceramic holding member which is disposed in said housing and has a centrally-disposed hole through it for holding said sensor element therein, a pressurizing member and powder filled volume occupying an insulating space between said holding member and said pressurizing member, wherein the top of said ceramic holding member has an inclined surface extending outward and downward directly from an upper opening end of said hole to a periphery of said sensor housing to provide a generally conical surface for causing continuous flow of said powder when said powder is filled and pressurized by said pressurizing member.

2. An oxygen concentration sensor claimed in claim 1 wherein said inclined surface on said holding member has a conical-section shaped top having an obtuse apex angle.

3. An oxygen concentration sensor claimed in claim 1, wherein said sensor element has a polygonal cross section, and wherein said holding hole is polygonal and said inclined surface comprises flat polygonal shaped surfaces extending outward and downward directly from said upper opening sides of said polygonal holding hole.

4. An oxygen concentration sensor claimed in claim 1, wherein said sensor element comprises a rectangular plate sensor element and said inclined surface is formed only in a direction in parallel with a shorter side of said plate sensor element such that the longer sides of said sensor element extends straight out in a horizontal manner from the central axis towards the periphery of said sensor housing.

5. An oxygen concentration sensor comprising:

a plate sensor element;

a housing having a longitudinal space and a first shoulder;

a holding member, having a longitudinally extending hole, an upper inclined surface and a bottom in contact with said first shoulder, for holding said sensor element in said hole, said hold member having a second shoulder formed in said longitudinal hole to facilitate installation of said sensor element in a pre-set position and orientation;

said plate sensor element disposed in said hole and having a flange portion in contact with said second shoulder; and a fixing member, including powder filled under pressure in a space formed by said longitudinal space and said holding member, for pressurizing said holding member and said plate sensor element; wherein said inclined surface provides a moderate boundary along an inner perimeter interface between said inclined surface and a periphery of said sensor element, wherein said moderate boundary allows said powder to flow outwards smoothly from said plate sensor element along said inclined surface.

6. An oxygen concentration sensor as claimed in claim 5, wherein said inclined surface of said holding member comprises a conical surface on said holding member having a conical-section shaped top.

7. An oxygen concentration sensor as claimed in claim 5, wherein said sensor element has a polygonal cross section, and wherein said hole is polygonal and said inclined surface comprises flat polygonal-shaped surfaces extending outward and downward directly from said upper opening sides of said polygonal hole.

8. An oxygen concentration sensor as claimed in claim 5, wherein said sensor element comprises a rectangular plate sensor element and said inclined surface is formed only in a direction in parallel with a shorter side of said plate sensor element such that the longer sides of said sensor element extend straight out in a horizontal manner from the central axis towards the periphery of said sensor housing.

9. An oxygen concentration sensor comprising:

a housing having a longitudinal space within which said housing provides support for a hold member disposed therein;

a plate sensor element disposed in said longitudinal space and having a flange portion;

said hold member having a longitudinally extending hole receiving said plate sensor element and an upper inclined surface extending outward and downward directly from said hole, with said upper inclined surface forming a moderate boundary along an interface between said inclined surface and said sensor element, said moderate boundary allowing said powder to flow outwards smoothly from said plate sensor element along said inclined surface said hold member holding said sensor element in said longitudinal space, said hold member having a shoulder formed in said hole for receiving said flange portion; and a fixing member, including powder filled under pressure in a remaining space formed by said longitudinal space and said hold member, for fixing said hold member and said plate sensor element in said longitudinal space.

10. An oxygen concentration sensor as claimed in claim 9, wherein said inclined surface of said hold member comprises a conical surface.

11. An oxygen concentration sensor as claimed in claim 9, wherein said inclined surface of said hold member comprises a parabolic surface.

12. An oxygen concentration sensor as claimed in claim 9, wherein said sensor element has a rectangular cross-section and said inclined surface is formed only in a direction in parallel with a shorter side of said plate sensor element.

13. An oxygen concentration sensor as claimed in claim 9, wherein said sensor element has an oval cross-section and said inclined surface is formed only in a direction in parallel with a shorter diameter of said plate sensor element.

14. An oxygen concentration sensor as claimed in claim 9, wherein said inclined surface of said hold member comprises a conical surface merged together with a flat annular surface placed around the outer edge of said conical surface.

* * * * *